US011712160B2

(12) United States Patent
Hirokawa et al.

(10) Patent No.: US 11,712,160 B2
(45) Date of Patent: Aug. 1, 2023

(54) IMAGE PROCESSING METHOD, IMAGE PROCESSING PROGRAM, IMAGE PROCESSING DEVICE, IMAGE DISPLAY DEVICE, AND IMAGE DISPLAY METHOD

(71) Applicant: NIKON CORPORATION, Tokyo (JP)

(72) Inventors: Mariko Hirokawa, Yokohama (JP); Yasushi Tanabe, Fujisawa (JP); Tomoharu Fujiwara, Gyoda (JP)

(73) Assignee: NIKON CORPORATION, Tokyo (JP)

( * ) Notice: Subject to any disclaimer, the term of this patent is extended or adjusted under 35 U.S.C. 154(b) by 374 days.

(21) Appl. No.: 16/957,873

(22) PCT Filed: Dec. 28, 2017

(86) PCT No.: PCT/JP2017/047379
§ 371 (c)(1),
(2) Date: Jun. 25, 2020

(87) PCT Pub. No.: WO2019/130583
PCT Pub. Date: Jul. 4, 2019

(65) Prior Publication Data
US 2020/0359888 A1    Nov. 19, 2020

(51) Int. Cl.
*A61B 3/10* (2006.01)
*A61B 3/00* (2006.01)
*A61B 3/12* (2006.01)
*G06T 7/00* (2017.01)

(52) U.S. Cl.
CPC ............ *A61B 3/102* (2013.01); *A61B 3/0025* (2013.01); *A61B 3/0041* (2013.01); *A61B 3/1233* (2013.01); *G06T 7/0002* (2013.01)

(58) Field of Classification Search
CPC ..... A61B 3/102; A61B 3/0025; A61B 3/0041; A61B 3/1233; G06T 7/0002
USPC ......................................... 351/205–206, 246
See application file for complete search history.

(56) References Cited

U.S. PATENT DOCUMENTS

| 8,419,186 | B2 | 4/2013 | Isogai et al. |
| 8,672,480 | B2 | 3/2014 | Isogai et al. |
| 2011/0170062 | A1 | 7/2011 | Isogai |
| 2012/0127428 | A1 | 5/2012 | Isogai |

(Continued)

FOREIGN PATENT DOCUMENTS

| JP | A 2010-233916 | 10/2010 |
| JP | 2014-014727 A | 1/2014 |

(Continued)

OTHER PUBLICATIONS

English machine translation only of Office Action issued in corresponding Japanese Patent Application No. 2019-562705 dated Feb. 16, 2021.

(Continued)

*Primary Examiner* — James R Greece
(74) *Attorney, Agent, or Firm* — Foley & Lardner LLP

(57) ABSTRACT

Predicting a non perfusion area.
An enhancement image processing section performs enhancement image processing on a fundus image of a subject eye to enhance vascular portions (304). A prediction processing section predicts a non perfusion area in the fundus image that has been subjected to the enhancement image processing (306 to 312). A generation section generates a non perfusion area candidate image (314).

7 Claims, 15 Drawing Sheets

(56) References Cited

U.S. PATENT DOCUMENTS

| | | | |
|---|---|---|---|
| 2014/0073917 A1* | 3/2014 | Huang | A61B 5/7207 600/427 |
| 2015/0374228 A1 | 12/2015 | Satake et al. | |
| 2017/0262988 A1 | 9/2017 | Ikegami et al. | |
| 2020/0359888 A1 | 11/2020 | Hirokawa et al. | |

FOREIGN PATENT DOCUMENTS

| | | | |
|---|---|---|---|
| JP | 5535905 B2 | 7/2014 | |
| JP | 6947226 B2 | 10/2021 | |
| WO | WO-2010131944 A2 * | 11/2010 | A61B 3/1233 |
| WO | WO-2014/040070 A1 | 3/2014 | |
| WO | WO-2016/151491 A1 | 9/2016 | |

OTHER PUBLICATIONS

Ooishi, "Course on how to take an image", Ophthalmological Care 2011 Extra Edition, 2011, ISBN 978-4-8404-3710-3, p. 112, non-official translation (Practical Lessons! A Course in OCT Imaging to Support Medical Diagnosis (Ophthalmological Care 2011 Special Supplement), 2011, 4 pages.

Croft et al., "Precise Montaging and Metric Quantification of Retinal Surface Area From Ultra-Widefield Fundus Photography and Fluorescein Angiography", Ophthalmic Surgery, Laser and Imaging Retina, vol. 45, No. 4, 2014, pp. 312-317.

Sim et al., "Patterns of Peripheral Retinal and Central Macula Ischemia in Diabetic Retinopathy as Evaluated by Ultra-widefield Fluorescein Angiography", Peripheral and Central Capillary Nonperfusion in Diabetes, American Journal of Ophthalmology, vol. 158, No. 1, Jul. 31, 2014, pp. 144-153.

Singer et al., "Targeted photocoagulation of peripheral ischemia to treat rebound edema", Clinical Ophthalmology, vol. 9, Feb. 13, 2015, pp. 337-341.

Jia et al., "Quantitative optical coherence tomography angiography of vascular abnormalities in the living human eye", Proceedings of the National Academy of Sciences of the United States of America, vol. 112, No. 18, May 5, 2015, pp. E2395-E2402.

Kang et al., "Ultra-Widefield Imaging for the Management of Pediatric Retinal Diseases", Journal of Pediatric Ophthalmology and Strabismus, 2013, vol. 50, No. 5, pp. 282-288 https://doi.org/10.3928/01913913-20130528-04 (posted on Jun. 4, 2013).

Rasta, et al., "Detection of retinal capillary nonperfusion in fundus fluorescein angiogram of diabetic retinopathy", Bio Impacts, vol. 5, No. 4, 2015, pp. 183-190.

Extended European Search Report issued in corresponding European Patent Application No. 17936466.6 dated Jul. 8, 2021.

Office action issued in corresponding Chinese Application No. 201780098008.8, dated Nov. 8, 2022.

Japanese Office Action issued in corresponding Japanese Patent Application No. 2021-151384, dated Aug. 9, 2022. with Machine translation (5 pages).

* cited by examiner

IMAGE PROCESSING METHOD, IMAGE PROCESSING PROGRAM, IMAGE PROCESSING DEVICE, IMAGE DISPLAY DEVICE, AND IMAGE DISPLAY METHOD

TECHNICAL FIELD

The present invention relates to an image processing method, an image processing program, an image processing device, an image display device, and an image display method.

BACKGROUND ART

Patent Document 1 discloses technology for detecting retinal vascular infraction in a test subject.

RELATED ART DOCUMENTS

Patent Documents

Japanese Patent No. 5535905

SUMMARY OF INVENTION

An image processing method of a first aspect of technology disclosed herein includes predicting a non perfusion area in a fundus image of a subject eye.

An image processing method of a second aspect of technology disclosed herein includes performing first image processing on a fundus image of a subject eye to extract a first non perfusion area candidate, performing second image processing on the fundus image to extract a second non perfusion area candidate, and extracting as a predicted non perfusion area any candidate that is both the first non perfusion area candidate and the second non perfusion area candidate.

An image processing program of a third aspect of technology disclosed herein causes a computer to execute the image processing method of the first aspect or the second aspect.

An image processing device of a fourth aspect of technology disclosed herein includes a storage device to store an image processing program for executing an image processing method in a processor, and a processing device configured to execute the image processing method by executing the image processing program stored in the storage device. In the image processing device the image processing method is the image processing method of the first aspect or the second aspect.

An image display device of a fifth aspect of technology disclosed herein includes a display section configured to display a non perfusion area predicted using the image processing method of the first aspect or the second aspect.

An image display method of a sixth aspect of technology disclosed herein includes receiving fundus image data of a fundus image of a subject eye and non perfusion area candidate image data of a non perfusion area candidate image obtained by performing image processing on the fundus image, and generating a screen in which the fundus image based on the fundus image data is displayed in a fundus image display field, and in which the non perfusion area candidate image based on the non perfusion area candidate image data is displayed in a non perfusion area candidate image display field.

An image display device of a seventh aspect of technology disclosed herein includes a display section configured to display on a same screen both a fundus image of a subject eye, and a non perfusion area candidate image obtained by performing image processing on the fundus image.

DESCRIPTION OF EMBODIMENTS

Detailed description follows regarding exemplary embodiments of the present invention, with reference to the drawings. In the following, for ease of explanation a scanning laser ophthalmoscope will be referred to as "SLO". Moreover, for ease of explanation optical coherence tomography will be referred to as "OCT".

Figure 1:
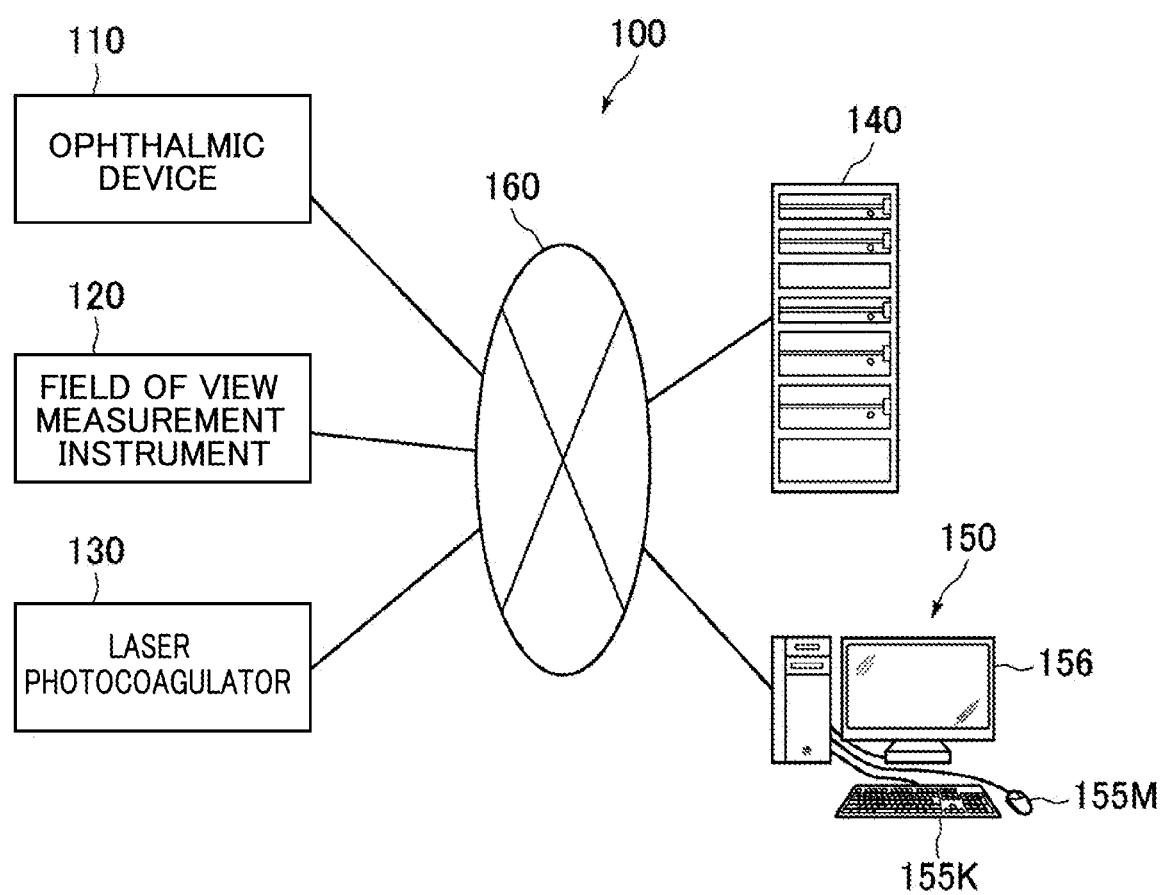
FIG. 1 is a block diagram of an ophthalmic system 100.

A configuration of an ophthalmic system 100 will now be described with reference to FIG. 1. As illustrated in the example of FIG. 1, the ophthalmic system 100 includes an ophthalmic device 110, a field of view measurement instrument 120, a laser photocoagulator 130, a management server device (hereafter referred to as "management server") 140, and an image display device (hereafter referred to as "image viewer") 150.

The ophthalmic device 110 acquires fundus images and tomographic images. The field of view measurement instrument 120 measures the field of view of a patient. The laser photocoagulator 130 uses a laser to coagulate pathological lesions on a fundus of the patient in order to suppress pathological progression. The management server 140 stores plural fundus images, obtained by imaging the fundus of plural patients using the ophthalmic device 110, in association with IDs of the patients, and predicts any non perfusion areas (NPAs) in a specified fundus image. The image viewer 150 displays an image of non perfusion area (NPA) candidates predicted by the management server 140.

These non perfusion areas (NPAs) are areas on a fundus where there is no blood flow or hardly any blood flow due to retina capillary vascular bed obstruction or the like, and may also be avascular areas (AVAs) which are areas on a fundus where there are no blood vessels or only sparse blood vessels.

The ophthalmic device 110, the field of view measurement instrument 120, the laser photocoagulator 130, the management server 140, and the image viewer 150 are all interconnected over a network 160.

The management server 140 is an example of an "image processing device" of the technology disclosed herein. The image viewer 150 is an example of an "image display device" of the technology disclosed herein.

Figure 2:
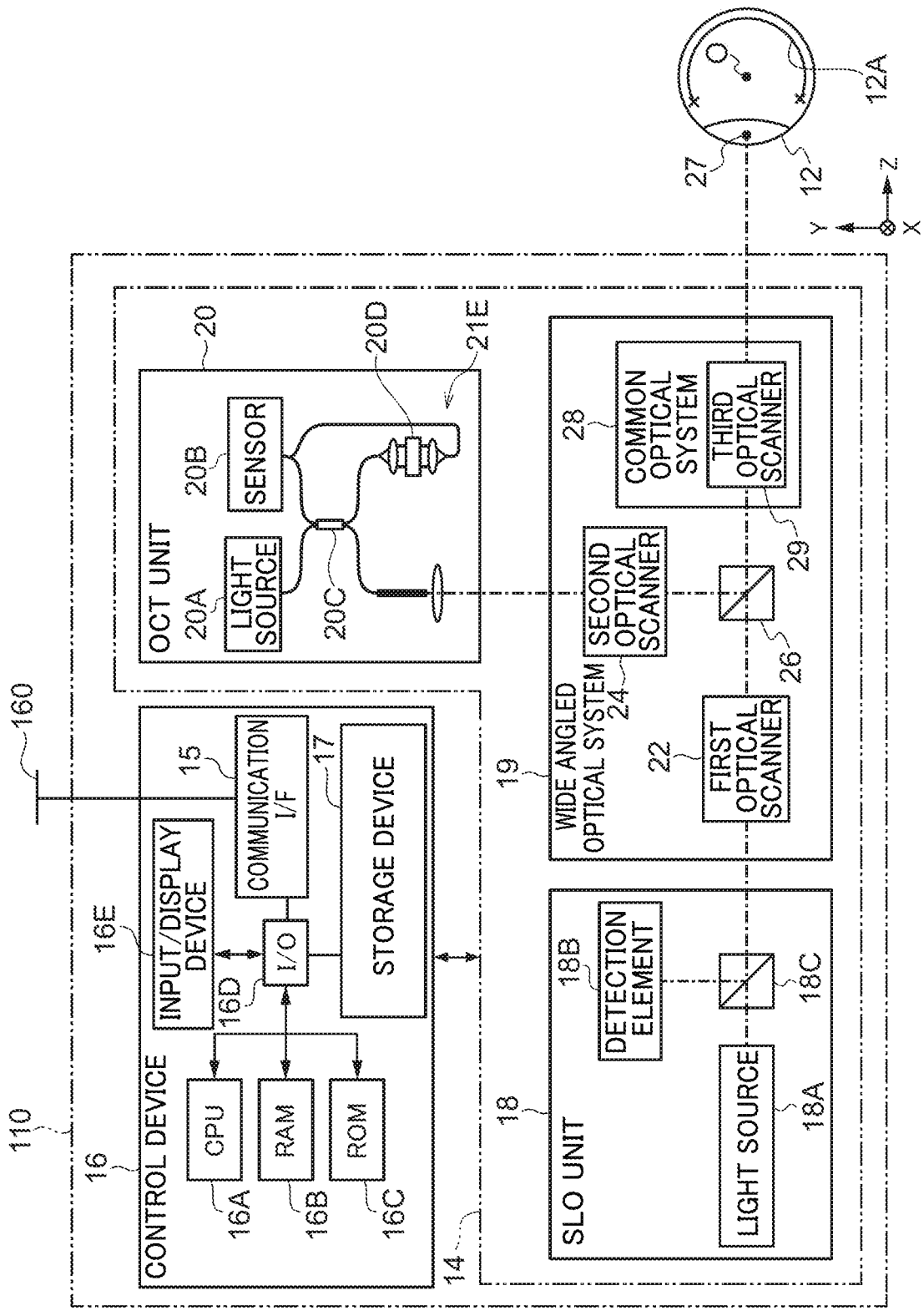
FIG. 2 is a schematic configuration diagram illustrating an example of an overall configuration of an ophthalmic device 110.

Next, description follows regarding a configuration of the ophthalmic device 110, with reference to FIG. 2. As illustrated in FIG. 2, the ophthalmic device 110 includes an imaging device 14 and a control device 16. The imaging device 14 images the fundus of a subject eye. The control device 16 is realized by a computer including a central processing unit (CPU) 16A, random access memory (RAM) 16B, read only memory (ROM) 16C, and an input/output (I/O) port 16D.

A storage device 17 is connected to the input/output (I/O) port 16D. Note that the storage device 17 is configured, for example, by non-volatile memory ((NVM) or a hard disk). The input/output (I/O) port 16D is connected to the network 160 through a communication interface (I/F) 15.

The control device 16 includes an input/display device 16E connected to the CPU 16A through the I/O port 16D. The input/display device 16E displays images obtained by imaging, and includes a graphical user interface to receive various instructions including an instruction to perform imaging. Examples of the graphical user interface include a touch panel display. Note that in the following, for convenience, "imaging" refers to a user using the ophthalmic device 110 to acquire an image of an imaging subject.

The imaging device 14 operates under control from the control device 16. The imaging device 14 includes a SLO unit 18, a wide angled optical system 19, and an OCT unit 20.

In the following description, when the ophthalmic device 110 is installed on a horizontal plane, the horizontal direction is referred to as the "X direction", a direction perpendicular to the horizontal direction is referred to as the "Y direction", and a direction connecting a pupil center 27 at the anterior segment of a subject eye 12 and an eyeball center O of the subject eye 12 is referred to as the "Z direction". Accordingly, the X direction, Y direction, and Z direction are mutually perpendicular directions.

The ophthalmic device 110 according to the present exemplary embodiment includes two functions, i.e. a first function and a second function, as examples of main functions that can be implemented by the ophthalmic device 110. The first function is a function (hereafter referred to as the SLO imaging system function) in which the ophthalmic device 110 is operated as a scanning laser ophthalmoscope (hereafter referred to as a SLO) to perform SLO imaging. The second function is a function (hereafter referred to as the OCT imaging system function) in which the ophthalmic device 110 operates in optical coherence tomography (hereafter OCT) to perform OCT imaging. Note that for ease of explanation the function of performing imaging by SLO will be referred to as the "SLO imaging system function". Moreover, for ease of explanation the function of performing imaging by OCT will be referred to as the "OCT imaging system function".

The SLO imaging system function is implemented by the control device 16, the SLO unit 18, and the wide angled optical system 19 in the configuration of the ophthalmic device 110. The SLO unit 18 includes a light source 18A, a detection element 18B, a dichroic mirror 18C and the like, and is configured to perform imaging of the fundus of the subject eye Namely, the fundus (for example an imageable region 12A) of the subject eye 12 is imaged as an imaging subject by operating the ophthalmic device 110 in the SLO imaging system function. Specifically, light from the SLO unit 18 (referred to hereafter as SLO light) is passed through the pupil of the subject eye 12 and onto the imageable region 12A by the wide angled optical system 19, while being scanned in the X direction (horizontal direction) by a first optical scanner 22 and being scanned in the Y direction (vertical direction) by a third optical scanner 29. A fundus image (SLO image (an UWFSLO fundus image, described later)) configured by this reflected light is acquired by the SLO unit 18. Note that the SLO imaging system function is a known function, and so detailed description thereof will be omitted. The imageable region 12A is within a range of approximately 200 degrees when converted into an internal illumination angle from the eyeball center O.

The OCT imaging system function is implemented by the control device 16, the OCT unit 20, and the wide angled optical system 19. The OCT unit 20 includes a reference optical system 21E including a light source 20A, a sensor (spectroscope) 20B, a fiber coupler 20C, and a polarized light adjuster 21D, and the like, and images plural tomographic regions in the fundus layer thickness direction. Namely, the ophthalmic device 110 images tomographic regions, which are regions in the fundus layer thickness direction (for example, the imageable region 12A), by being operated in the OCT imaging system function. Specifically, the light from the light source 20A of the OCT unit 20 (hereafter referred to as signal light (LS)) is branched by the fiber coupler 20C. One signal light therefrom is passed through the pupil of the subject eye 12 and onto the imageable region 12A by the wide angled optical system 19, while being scanned in the X direction (horizontal direction) by the second optical scanner 24 and being scanned in the Y direction (vertical direction) by the third optical scanner 29. The one signal is reflected at the tomographic region, and the reflected light proceeds through the fiber coupler 20C and along a path incident to the sensor 20B.

The optical path length of the signal light (LS) is determined by the distance from the light source 20A to the tomographic region, and by the distance from the tomographic region to the sensor 20B.

Note that in the signal light, the reflected light that has been reflected by the tomographic region and is incident to the sensor 20B is in particular called return light.

Moreover the other signal light branched by the fiber coupler 20C has a light path length adjusted by the polarized light adjuster 21D, and proceeds along an optical path incident to the sensor 20B.

Note that the other signal light, namely the signal light proceeding from the light source 20A, through the fiber coupler 20C and the polarized light adjuster 21D, to the sensor 20B is referred to as reference light (LR).

The return light and the reference light interfere at the sensor 20B to form incident interference light. The sensor 20B detects each of the spectral components of the interference light. The control device 16 uses the detection results of the sensor 20B to acquire a tomographic image (hereafter referred to as an "OCT image") illustrating a tomographic region.

The acquired SLO image and OCT image are transmitted, together with the patient ID, through the communication interface (I/F) 15 to the management server 140 over the network 160.

Figure 3:
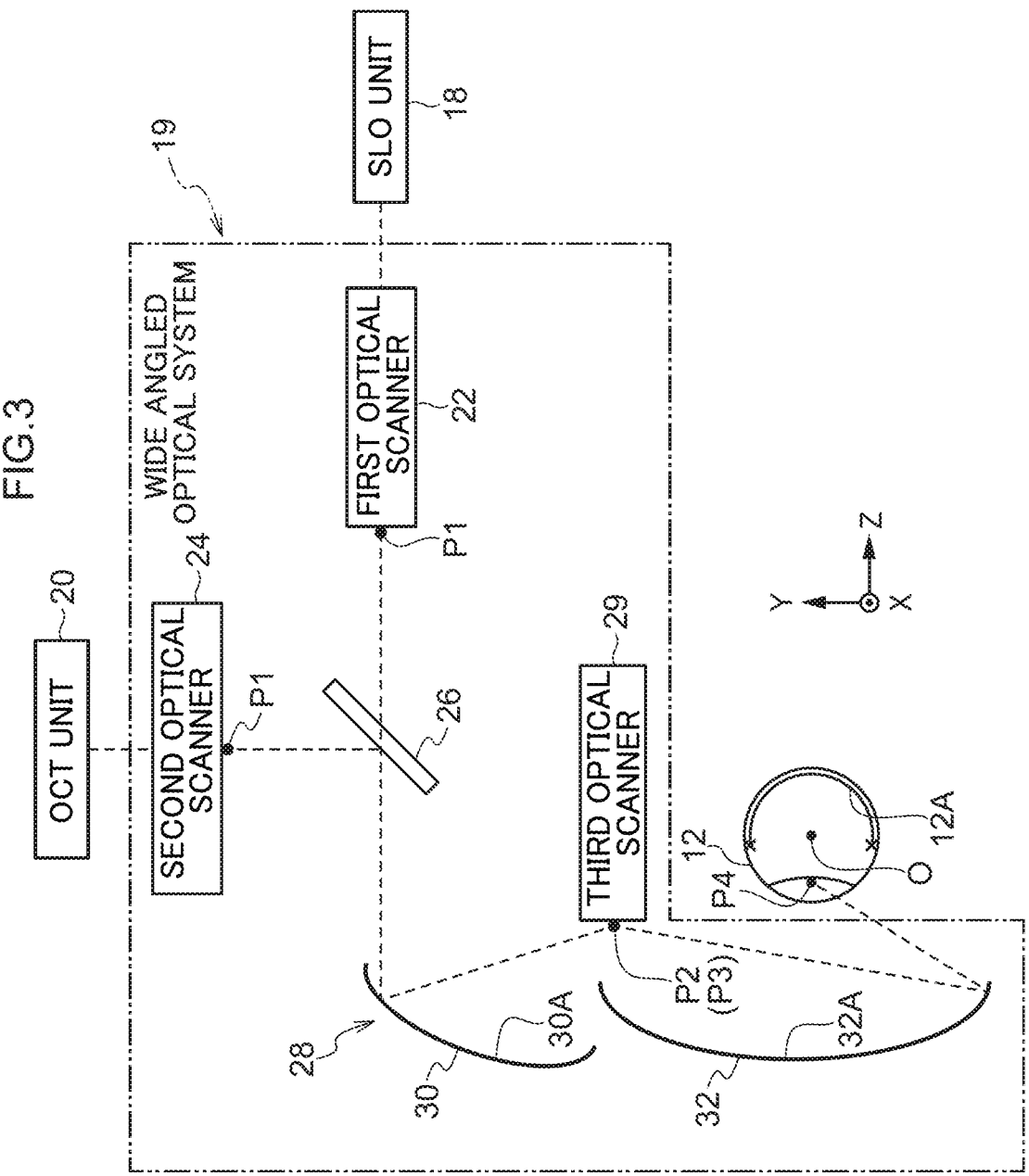
FIG. 3 is a schematic diagram illustrating an example of a schematic configuration of a wide angled optical system 19 included in the ophthalmic device 110.

Next, description follows regarding a configuration of the wide angled optical system 19 included in the ophthalmic device 110, with reference to FIG. 3. As illustrated in FIG. 3, a common optical system 28 includes, in addition to the third optical scanner 29, a slit mirror 30 and an elliptical mirror 32. Note that side view end faces are illustrated of a dichroic mirror 26, the slit mirror 30, and the elliptical mirror 32. Note that a configuration may also be adopted in which plural lens groups are employed instead of the common optical system 28, the slit mirror 30, and the elliptical mirror 32.

The slit mirror 30 includes an elliptical shaped first reflection surface 30A. The first reflection surface 30A includes a first focal point P1 and a second focal point P2. The elliptical mirror 32 also includes an elliptical shaped second reflection surface 32A. The second reflection surface 32A includes a first focal point P3 and a second focal point P4.

The slit mirror 30, the elliptical mirror 32, and the third optical scanner 29 are arranged so that the first focal point P3 and the second focal point P2 lie at a common position on the third optical scanner 29. Moreover, the slit mirror 30, the elliptical mirror 32, and the third optical scanner 29 are arranged so that the second focal point P4 is positioned at a central portion of the pupil of the subject eye 12. Furthermore, the first optical scanner 22, the second optical scanner 24, and the slit mirror 30 arranged so that the first focal point P1 is positioned on the first optical scanner 22 and the second optical scanner 24.

Namely, the first optical scanner 22, the second optical scanner 24, and the third optical scanner 29 are arranged at conjugate positions to the central portion of the pupil of the subject eye 12.

Note that the wide angled optical system 19, as well as being a wide angled optical system employing an elliptical mirror, may also be a wide angled optical system combining an optical system employing a wide angled lens in combination with plural lenses.

In the present exemplary embodiment, a field of view (FOV) of the fundus is an angle of a fundus region over a wide range from the fundus center to the fundus periphery that is observable by the wide angled optical system 19 illustrated in FIG. 3. The size of this wide range fundus region is determined by the internal illumination angle and the external illumination angle.

The external illumination angle is an illumination angle of light from the ophthalmic device 110 side, namely from the exterior of the subject eye 12. Namely, the external illumination angle is the angle of scanned light onto the fundus of the subject eye 12 heading toward a pupil center 27 of the subject eye 12 (namely, a center point of the pupil as viewed face-on (see also FIG. 2)). The external illumination angle is equivalent to the angle of light reflected from the fundus so as to head out from the pupil center 27 and be emitted from the subject eye 12 toward the ophthalmic device 110.

The internal illumination angle is an illumination angle of light effectively imaged when the scanning light is illuminated onto the fundus of the subject eye 12, with respect to the eyeball center O of the subject eye 12 as a reference position. Although an external illumination angle A and an internal illumination angle B are in a correspondence relationship, since in the following description a description of an ophthalmic device is given, the external illumination angle is employed as an illumination angle corresponding to the field of view angle of the fundus.

The ophthalmic device 110 images within the imageable region 12A (see FIG. 2), which is a fundus region of the subject eye 12. The imageable region 12A is the maximum scannable region with the scanning light using the wide angled optical system 19, and the external illumination angle A is approximately 160 degrees (corresponding to an internal illumination angle of approximately 200 degrees). The SLO image obtained by imaging the imageable region 12A is referred to as an UWFSLO image. Note that UWF is an abbreviation for Ultra Widefield.

Figure 4:
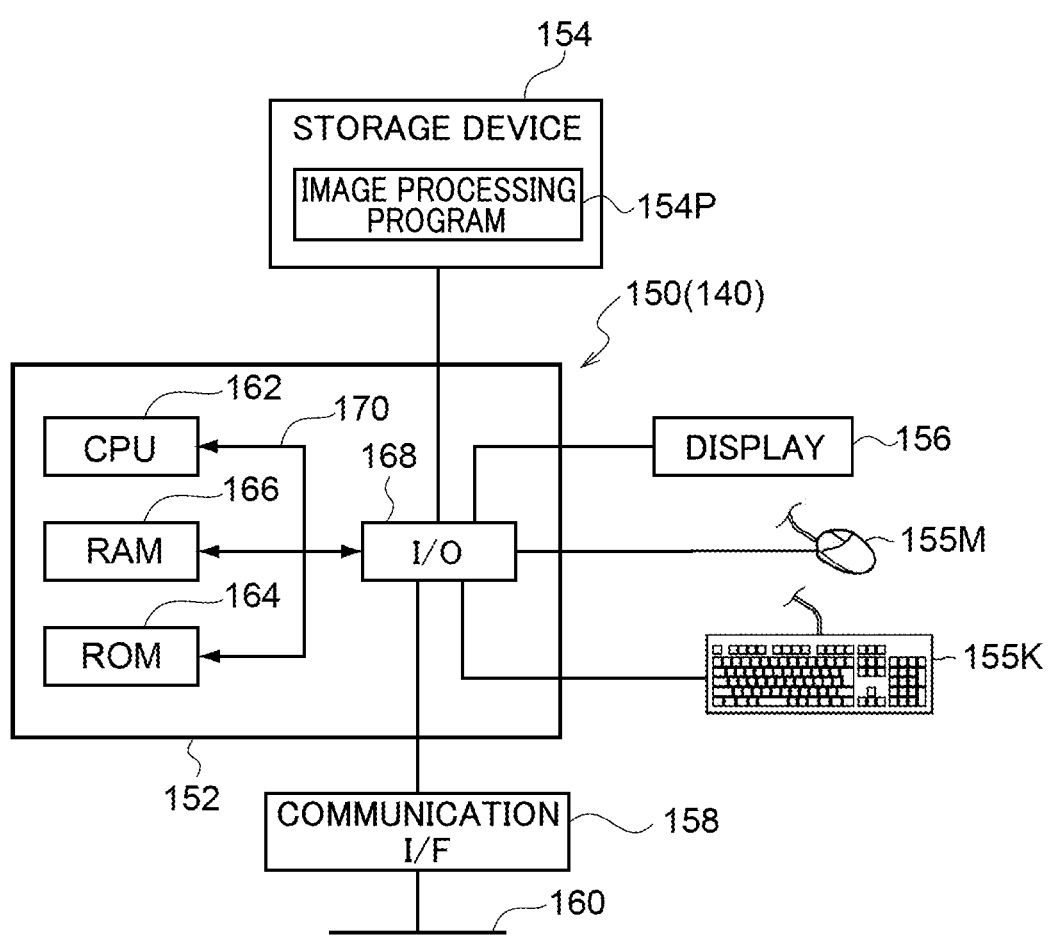
FIG. 4 is a block diagram of a configuration of an electrical system for an image viewer 150 and a management server 140.

Next, description follows regarding a configuration of an electrical system of the image viewer 150, with reference to FIG. 4. As illustrated in FIG. 4, the image viewer 150 is equipped with a computer main unit 152. The computer main unit 152 includes a CPU 162, RAM 166, ROM 164, and an input/output (I/O) port 168. A storage device 154, a display 156, a mouse 155M, a keyboard 155K, and a communication interface (I/F) 158 are connected to the input/output (I/O) port 168. The storage device 154 is, for example, configured by non-volatile memory. The input/output (I/O) port 168 is connected to the network 160 through the communication interface (I/F) 158. This thereby enables the image viewer 150 to communicate with the ophthalmic device 110 and the management server 140.

The display 156 of the image viewer 150 is an example of a "display section" of the technology disclosed herein.

The configuration of the electrical system of the management server 140 is, similarly to the configuration of the electrical system of the image viewer 150, equipped with a computer main unit 152, including the CPU 162, the RAM 166, the ROM 164, and the input/output (I/O) port 168, and with the storage device 154, the display 156, the mouse 155M, and the keyboard 155K that are connected to the input/output (I/O) port 168.

The CPU 162 of the management server 140 is an example of an "image processing device" of the technology disclosed herein.

Fundus image data for test subjects and an image processing program 154P are stored in the storage device 154 of the management server 140.

Although a description follows of a case in which the image processing program 154P is stored in the storage device 154, the technology disclosed herein is not limited thereto, and the image processing program 154P may be stored on the ROM 164.

The image processing program 154P is an example of an image processing program according to technology disclosed herein.

Elements corresponding to the display 156, the mouse 155M, and the keyboard 155K of the image viewer 150 may be omitted for a configuration of the electrical system of the management server 140.

Figure 5:
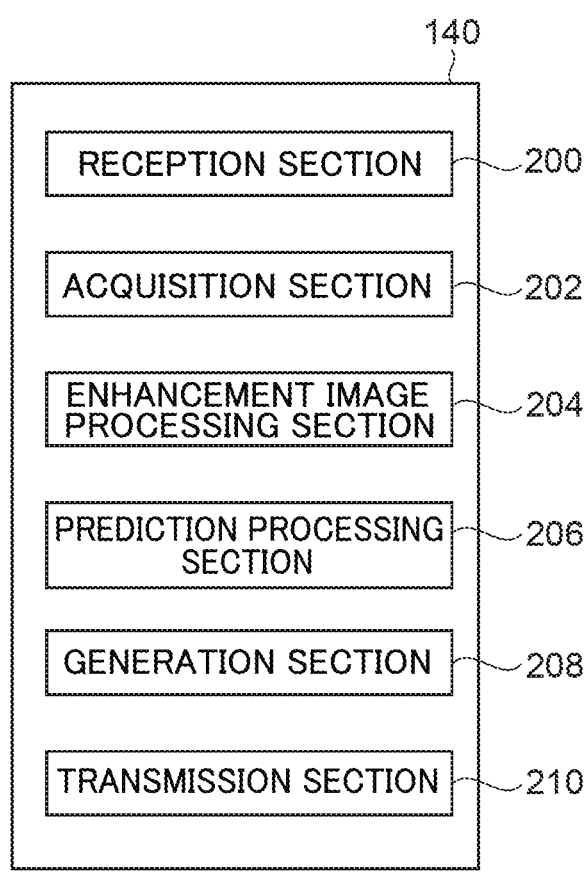
FIG. 5 is a block diagram of functions of the management server 140.

Next, description follows regarding various functions implemented by the CPU 162 of the management server 140 executing the image processing program 154P, with reference to FIG. 5. The image processing program 154P is equipped with a reception function, an acquisition function, an enhancement image processing function, a prediction processing function, a generation function, and a transmission function. The CPU 162 functions as a reception section 200, an acquisition section 202, an enhancement image processing section 204, a prediction processing section 206, a generation section 208, and a transmission section 210 as illustrated in FIG. 5 by the CPU 162 executing the multi-function image processing program 154P.

The enhancement image processing section 204, the prediction processing section 206, and the generation section 208 may be configured by an integrated image processing chip (an IC, a hardware configuration such as circuit, or the like).

Next, description follows regarding overall operation of the ophthalmic system 100 illustrated in FIG. 1.

First, the ophthalmic system 100 collects basic information about the subject eye 12 of a patient in order to perform a diagnosis on the subject eye 12 of the patient (see FIG. 2). More specifically, the eye axial length etc. is measured using a non-illustrated eye axial length measurement instrument, or the like. Furthermore, on instruction by a doctor, the patient goes to a room where the field of view measurement instrument 120 is installed. The field of view measurement instrument 120 measures a visible range (field of view map) by looking at responses of the patient when a light stimulus is imparted to the retina. The field of view measurement instrument 120 transmits the measured field of view map to the management server 140 together with the patient ID. The management server 140 stores the field of view map in the storage device 154 (see FIG. 4) in association with the patient ID. On instruction by the doctor, the patient then goes to a room where the ophthalmic device 110 is installed. The ophthalmic device 110 images the subject eye 12 of the patient to acquire the fundus image (SLO image (UWFSLO fundus image) and OCT image). The ophthalmic device 110 transmits the acquired fundus image to the management server 140 together with the patient ID. The management server 140 stores the fundus image in the storage device 154 associated with the patient ID.

When examining the subject eye 12 of the patient, the doctor employs the fundus image of the subject eye 12, and sometimes employs information about whether or not there is a non perfusion area on the fundus. First, the patient ID is input to the image viewer 150, then the image viewer 150 acquires the fundus image of the patient from the management server 140, and the acquired fundus image is displayed on the display 156. An instruction to generate a non perfusion area candidate image for the fundus image being displayed is then transmitted from the image viewer 150 to the management server 140.

The management server 140 transmits image data for the generated non perfusion area candidate image based on the specified fundus image to the image viewer 150.

The non perfusion area candidate image is a fundus image with any predicted non perfusion areas displayed so as to be superimposed thereon.

Although described in detail later, the management server 140 reads the specified fundus image from the storage device 154, predicts any non perfusion areas in the read fundus image, and generates a final image of candidate areas for non perfusion areas (either as a non perfusion area candidate image or a candidate group image), and transmits the image data for the generated final image to the image viewer 150.

The image viewer 150 receives the image data for the non perfusion area candidate image using the communication interface I/F 158, and displays the non perfusion area candidate image on the display 156.

The fundus image is an UWFSLO fundus image imaged with the ophthalmic device 110, and enables the prediction of whether or not there are any NPAs, serving as targets, present across a wide range of the fundus. Obviously there is no limitation to using an UWFSLO fundus image, and the NPAs may be predicted using fundus images of the same patient (previously imaged UWFSLO fundus images, fundus images imaged with another instrument, or the like).

The doctor diagnoses the subject eye 12 of the patient based on the non perfusion area candidate image displayed on the display 156. If there is no problem with the subject eye 12 then the consultation is ended. However, in cases in which there is a problem with the subject eye 12 and the doctor has diagnosed a need for an OCT image, then a tomographic image of a fundus layer needs to be acquired using the ophthalmic device 110, and so an instruction to perform imaging by OCT may be output through the image viewer 150 to the ophthalmic device 110.

When instructed to perform imaging by OCT, the ophthalmic device 110 transmits an OCT image acquired with the ophthalmic device 110 to the management server 140 together with the patient ID. The management server 140 stores the OCT image in the storage device 154 associated with the patient ID, and also transmits the OCT image to the image viewer 150.

Figure 18:
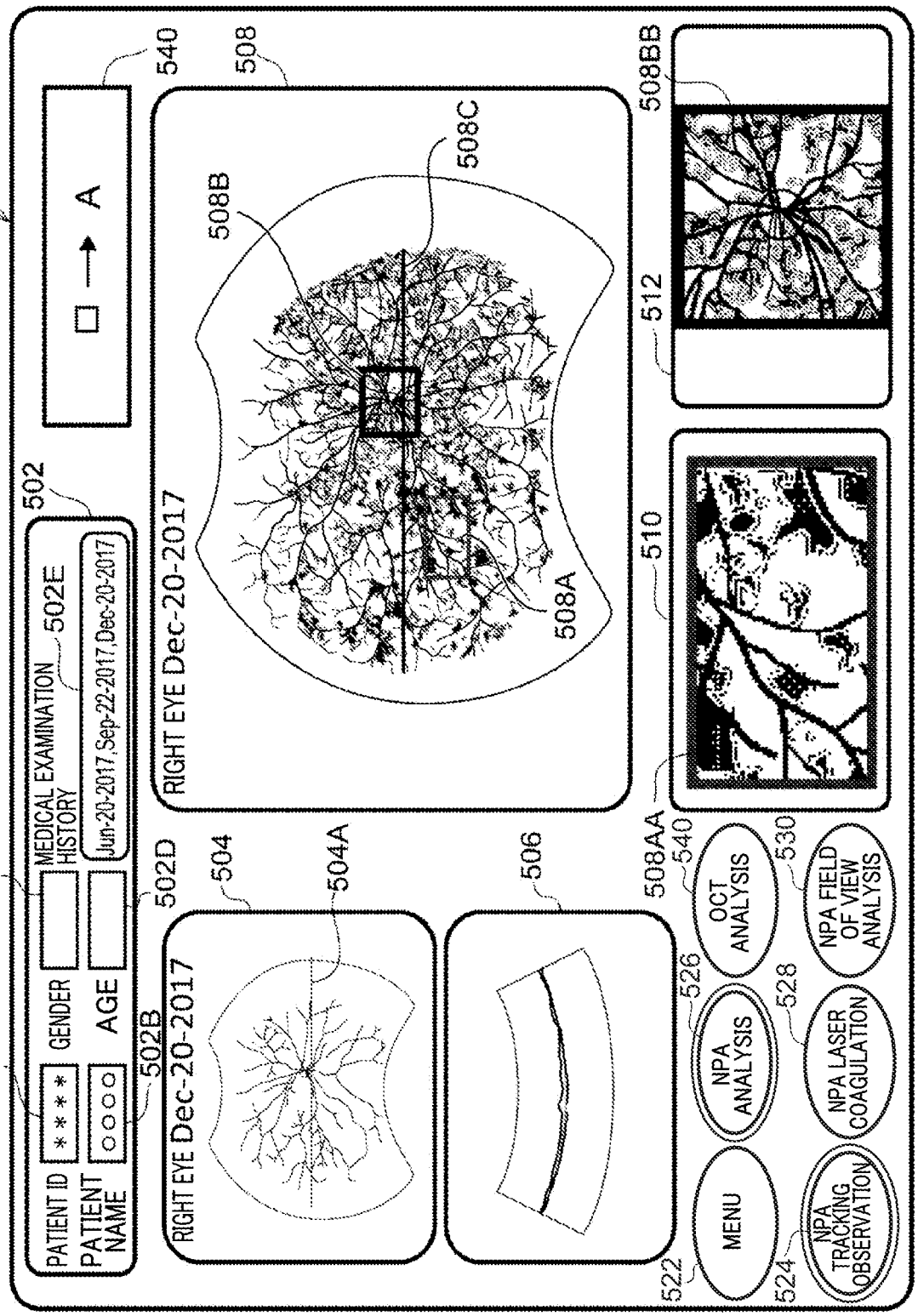
FIG. 18 is a diagram illustrating a screen 500 of a display 156 of the image viewer 150.

Although described in detail later, briefly the image viewer 150 performs screen display in various display modes on the screen 500 of the display 156 of the image viewer 150, as illustrated in FIG. 18.

Figure 6:
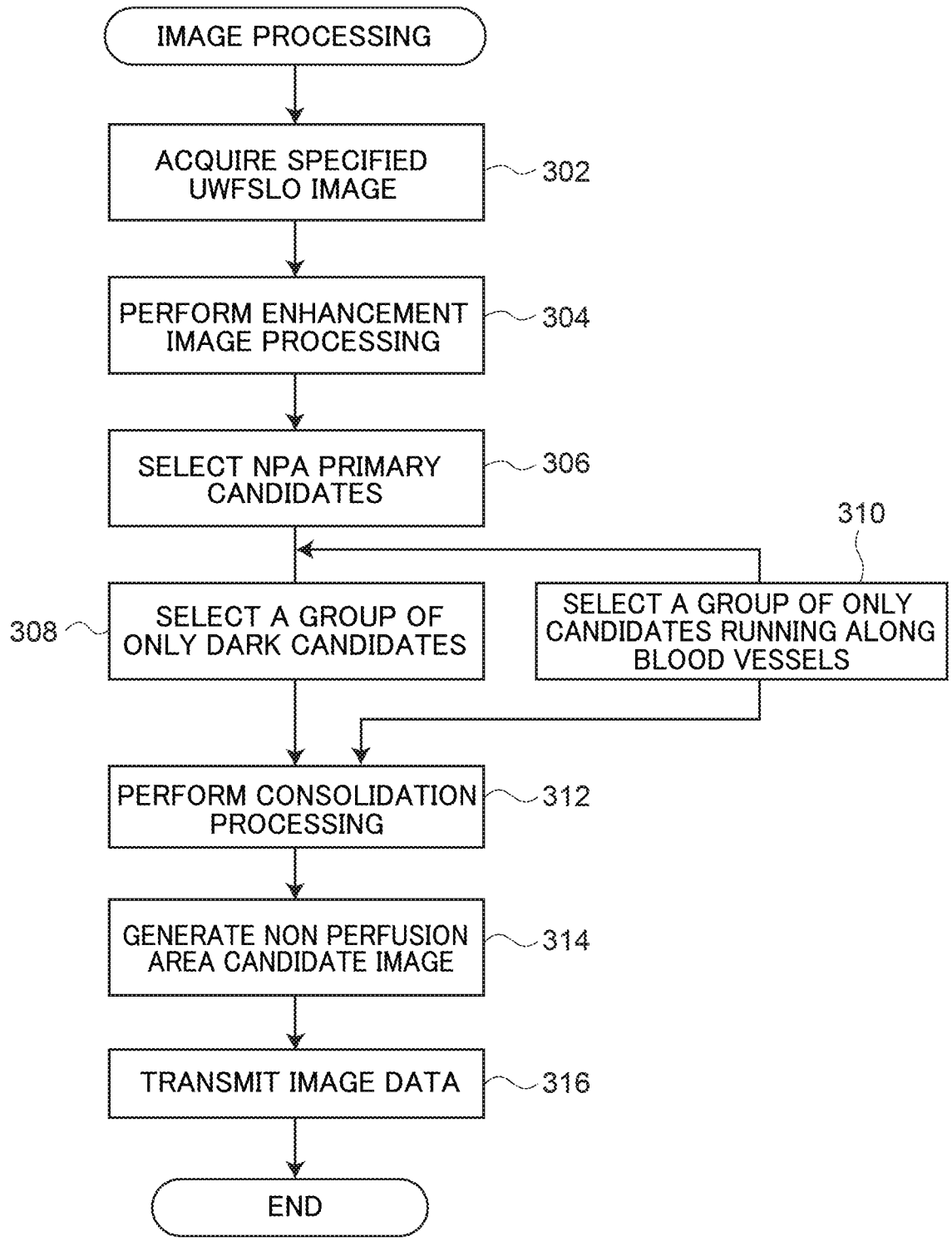
FIG. 6 is a flowchart illustrating an image processing program executed by a CPU 162 of the management server 140.

Next, description follows regarding the image processing program executed by the CPU 162 of the management server 140, with reference to FIG. 6. The image processing illustrated in FIG. 6 is implemented by the CPU 162 of the management server 140 executing the image processing program 154P.

The image processing illustrated in FIG. 6 is an example of an "image processing method" of technology disclosed herein.

The image processing program 154P is started when the reception section 200 (see also FIG. 5) has received command data from the image viewer 150. The command data is issued from the image viewer 150, and relates to a command to generate a non perfusion area (NPA) candidate image from the specified UWFSLO image, and to transmit image data for the non perfusion area (NPA) candidate image to the image viewer 150.

Figure 7:
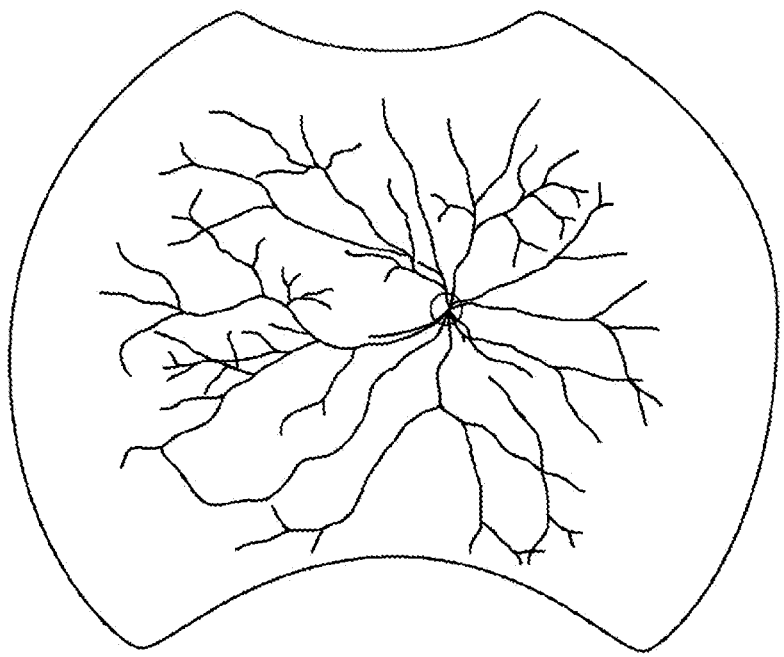
FIG. 7 is a diagram illustrating a fundus image (SLO image (UWFSLO fundus image)).

When the image processing program 154P has started, at step 302 the acquisition section 202 acquires the specified UWFSLO image from out of the plural UWFSLO images stored in the storage device 154 in association with the plural respective patient IDs. The UWFSLO images, as illustrated in FIG. 7, include structures such as retina vascular structures, the optic nerve head, and the like.

Next at step 304, the enhancement image processing section 204 performs enhancement image processing on the acquired UWFSLO image to enhance vascular portions thereof. This processing is processing performed to make the blood vessels including capillary blood vessels more prominent in order to predict non perfusion areas (NPAs) with good precision.

Figure 8:
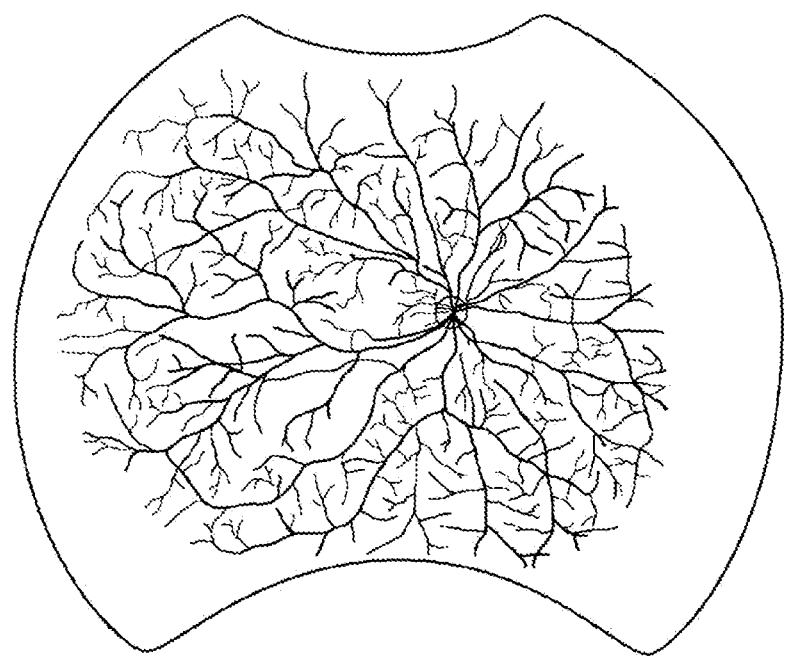
FIG. 8 is a diagram illustrating a fundus image in which capillary blood vessels have been enhanced.

The enhancement image processing may employ various methods, such as enhancement processing in which an image histogram is employed, as in histogram averaging and contrast limited adaptive histogram equalization (CLAHE), or alternatively such as contrast conversion processing based on gradation conversion, frequency enhancement processing for a particular frequency band such as processing by unsharp masking, deconvolution processing such processing by Weiner filter, morphology processing to enhance the shape of vascular portions, or the like. Preferably histogram averaging or adaptive histogram equalization is employed therefor. The blood vessels are enhanced by the enhancement image processing, and the capillary blood vessels are also enhanced as illustrated in FIG. 8.

This enables the non perfusion areas (NPAs) to be predicted with good precision from the UWFSLO image in which the blood vessels have been enhanced. Thus in the technology disclosed herein, at the next steps 306 to 312, the prediction processing section 206 predicts plural non perfusion areas (NPAs) in the UWFSLO image in which the blood vessels have been enhanced.

Specifically, at step 306, the prediction processing section 206 selects primary candidates for non perfusion areas (NPAs). More specifically, the prediction processing section 206 extracts plural pixels of a first darkness or darker from the UWFSLO image in which the blood vessels have been enhanced (see FIG. 8), and selects as primary candidates for non perfusion areas (NPAs) a single or plural areas having a surface area of a prescribed surface area or greater of contiguous pixels of the first darkness or darker.

The pixels of the first darkness or darker referred to here are pixels for which the pixel value of the respective pixel is a first specific value or lower.

Note that as the pixel values, for example, brightness values expressing lightness may be employed therefor, however, values expressing at least one out of saturation or hue may also be employed therefor instead of brightness values, or as well as the brightness values. A primary candidate is an example of a "first non perfusion area candidate" of the technology disclosed herein.

Figure 9:
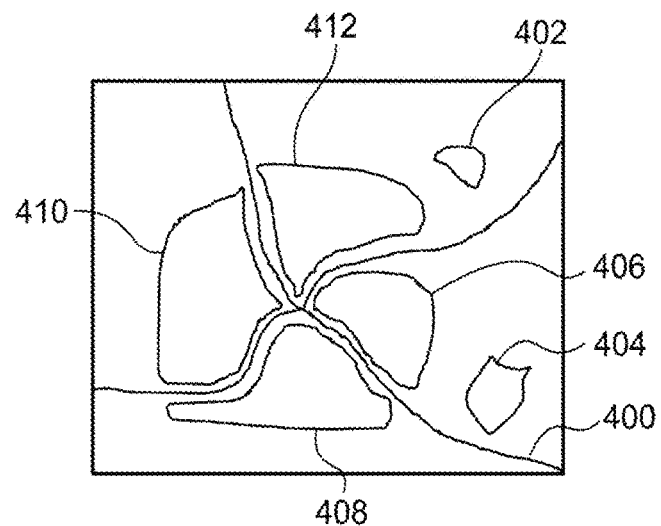
FIG. 9 is an enlarged schematic image of a portion of an UWFSL image illustrating a simplified representation of results of processing of step 306.

FIG. 9 is a schematic image illustrating an enlarged display of a portion of an UWFSLO image as a simplified representation of results of processing of step 306. There are six primary candidates 402, 404, 406, 408, 410, 412 for the non perfusion areas (NPAs) shown together with blood vessels 400 in FIG. 9.

After step 306 the image processing proceeds to step 308 and step 310.

At step 308, from the single or plural primary candidates of the non perfusion areas (NPAs), the prediction processing section 206 selects only dark candidates from the primary candidates based on a respective average value of the pixel values in each of the candidate areas. Specifically, the prediction processing section 206 calculates an average value of the pixel values in each of the areas of the single or plural primary candidates of non perfusion areas (NPAs), and selects as a dark area a single or plural candidate whose calculated average value is smaller than a second specific value. The second specific value is a value of a specific value smaller than the first specific value. Namely, only candidates that are dark areas having a darkness that is a second darkness darker than the first darkness, or darker (i.e. candidates having a specific average pixel value or less), are extracted from the primary candidates of the first darkness, to yield first secondary candidates.

The first secondary candidates are examples of "second non perfusion area candidates" of technology disclosed herein.

Figure 10:
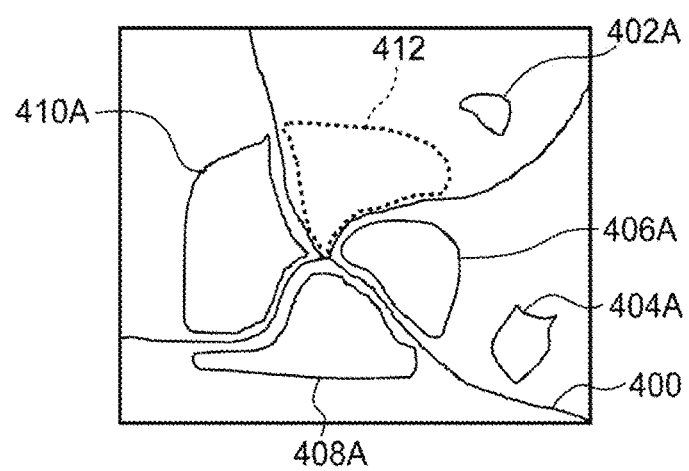
FIG. 10 is a diagram illustrating exclusion of a candidate 412 from six primary candidates 402, 404, 406, 408, 410, 412 of FIG. 9.

When the processing of step 308 is executed after the processing of step 306, for example as illustrated in FIG. 10, the primary candidate 412 is excluded from the six primary candidates 402, 404, 406, 408, 410, 412 (see FIG. 9) extracted at step 306. This thereby narrows down the candidates to the first secondary candidates 402A, 404A, 406A, 408A, 410A.

At step 310, the prediction processing section 206 narrows down the plural primary candidates for non perfusion areas (NPAs) to only areas having blood vessels running alongside. More specifically, first the prediction processing section 206 (1) extracts blood vessels. The blood vessels are extracted based on the pixel values using a method such as morphology processing or binarization or the like. Note that the areas extracted thereby are referred to as vascular areas. Then the prediction processing section 206 (2) uses a method such as distance conversion to compute a distance between such vascular areas and the peripheral edges of a single or plural primary candidates for non perfusion areas (NPAs) or for, or of each area group of candidate groups for non perfusion areas (NPAs), and selects areas in which this computed distance is within a fixed range.

The fixed range referred to here is a first range that is larger than a first specific distance, but smaller than a second specific distance larger than the first specific distance (namely, cases in which the areas have blood vessels running alongside).

Figure 11:
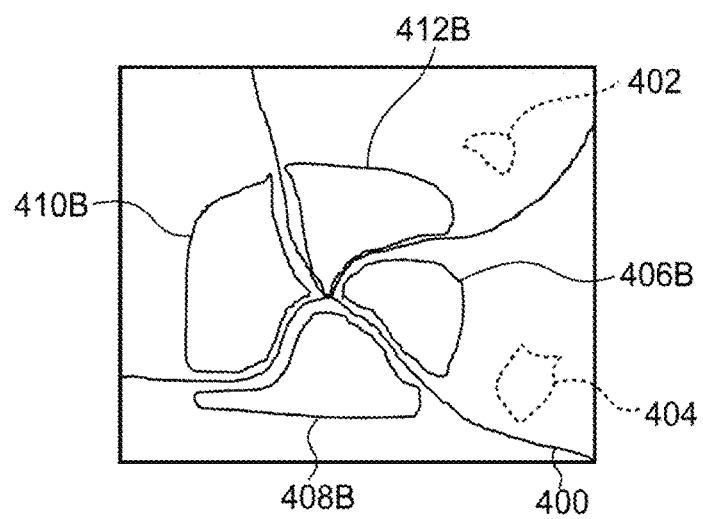
FIG. 11 is a diagram illustrating exclusion of candidates 402, 404 from the six primary candidates 402, 404, 406, 408, 410, 412 of FIG. 9.

Thus at step 310, the prediction processing section 206 extracts from the primary candidates areas for which a distance to blood vessels is a first distance or lower, as second secondary candidates areas. The candidates 402, 404 are, for example, accordingly excluded as they are not areas having blood vessels running alongside, as illustrated in FIG. 11. This thereby narrows down the candidates to the second secondary candidates 406B, 408B, 410B, 412B as candidates having blood vessels running alongside.

Figure 12:
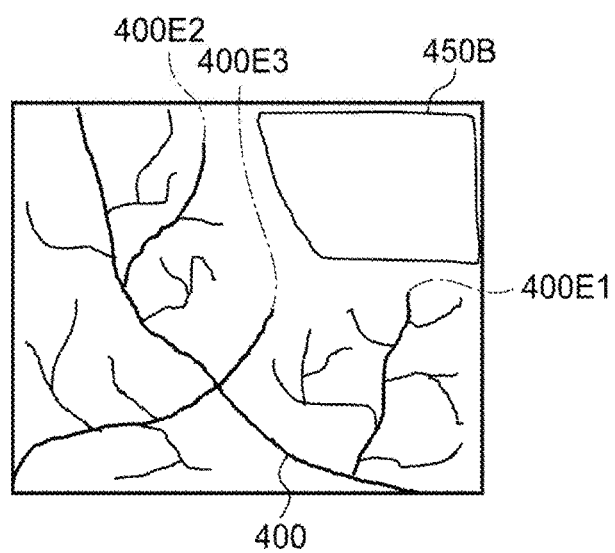
FIG. 12 is a diagram illustrating a candidate 450B narrowed down to run along terminal ends 400E1, 400E2, 400E3 of blood vessels.

Note that for the second secondary candidates, as illustrated in FIG. 12, an area 450B that is a fixed range away from blood vessel terminal ends 400E1, 400E2, 400E3 may be employed as a second secondary candidate.

The second secondary candidates are an example of "second non perfusion area candidates" of the technology disclosed herein.

Step 308 and step 310 may be executed one after each other, or may be executed at the same time as each other. The image processing proceeds to step 312 after the processing of step 308 and step 310 has been completed.

At step 312, the prediction processing section 206 performs consolidation processing to consolidate the first secondary candidates and the second secondary candidates. Specifically, areas are extracted that are members of the first secondary candidates (plural dark areas) and are also members of the second secondary candidates (plural areas having the blood vessels running alongside), and identifies these as predicted non perfusion areas.

Figure 13:
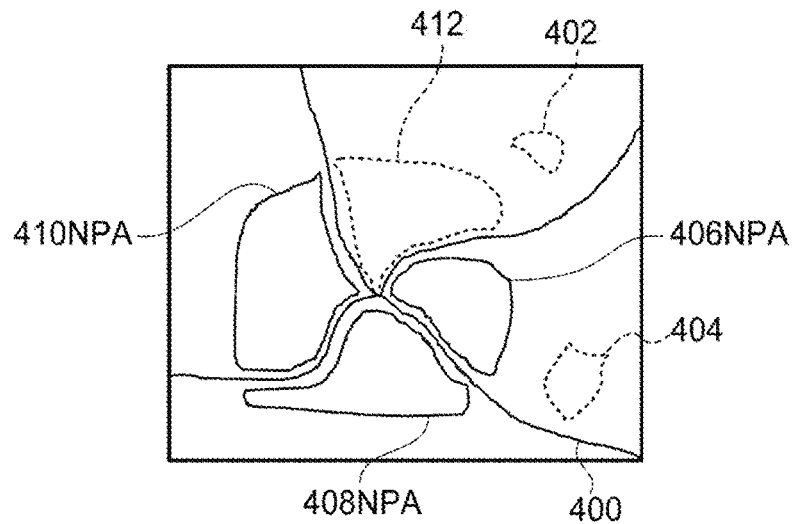
FIG. 13 is a diagram illustrating exclusion of candidates 402, 404, 412 from the six primary candidates 402, 404, 406, 408, 410, 412 of FIG. 9.
Figure 14:
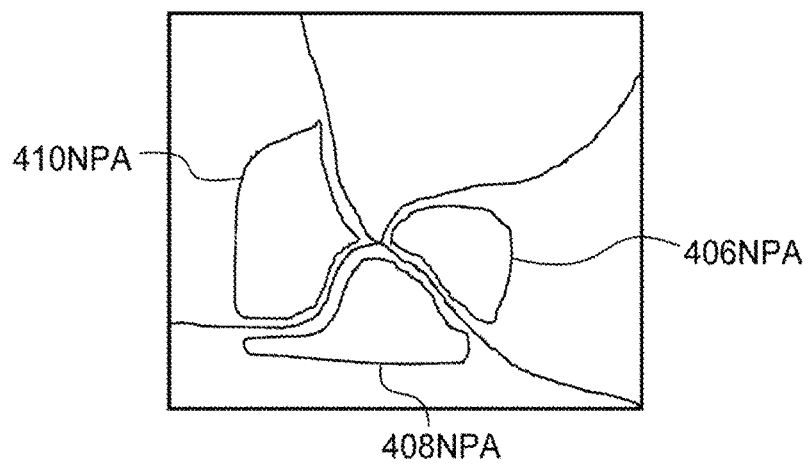
FIG. 14 is a diagram illustrating predicted non perfusion areas 406NPA, 408NPA, 410NPA.

In the example of FIG. 9, the six primary candidates 402, 404, 406, 408, 410, 412 are obtained as non perfusion areas (NPAs) at step 306. However, as illustrated in FIG. 13, the candidate 412 is excluded at step 308, and the candidates 402, 404 are excluded at step 310. Thus, as illustrated in FIG. 14, the candidates 406, 408, 410 are identified at step 312 as predicted non perfusion areas 406NPA, 408NPA, 410NPA.

Figure 15:
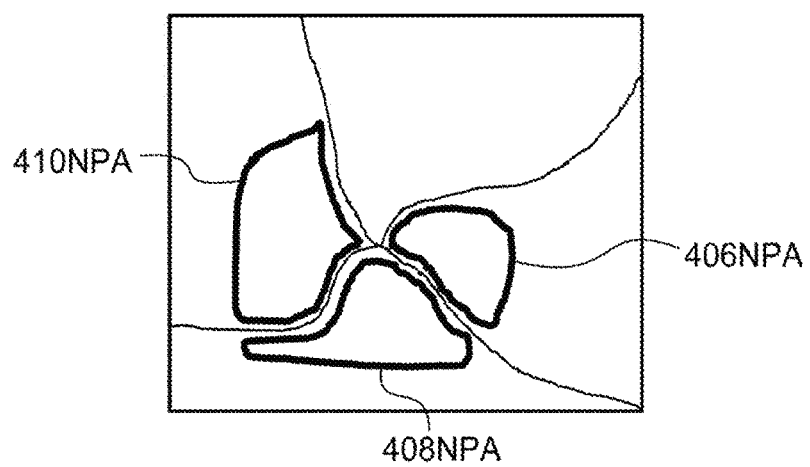
FIG. 15 is a diagram illustrating an appearance when colored borders have been applied to the periphery of the predicted non perfusion areas 406NPA, 408NPA, 410NPA.

Next at step 314, the generation section 208 applies a colored border to the periphery of the predicted non perfusion areas in the UWFSLO image to generate the non perfusion area candidate image. The non perfusion area candidate image refers to a fundus image in which predicted non perfusion areas are displayed superimposed on the UWFSLO image so as to enable positions of the predicted non perfusion areas on the UWFSLO image to be easily ascertained. The predicted non perfusion areas are displayed surrounded by borders in the image in order to enable the positions of the predicted non perfusion areas on the UWFSLO image to be easily ascertained. As an example of such display, part of the UWFSLO image is, as illustrated in FIG. 15, displayed with colored borders applied to the peripheries of the predicted non perfusion areas 406NPA, 408NPA, 410NPA.

Figure 16:
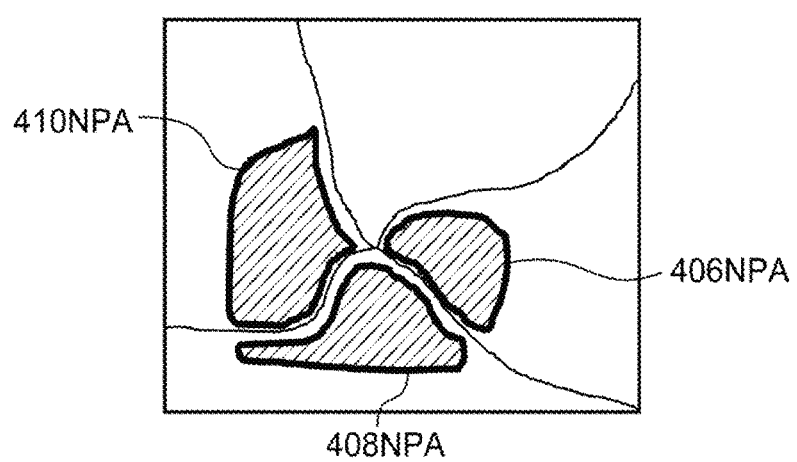
FIG. 16 is a diagram illustrating an appearance when light color shading has been applied to the predicted non perfusion areas 406NPA, 408NPA, 410NPA.
Figure 17:
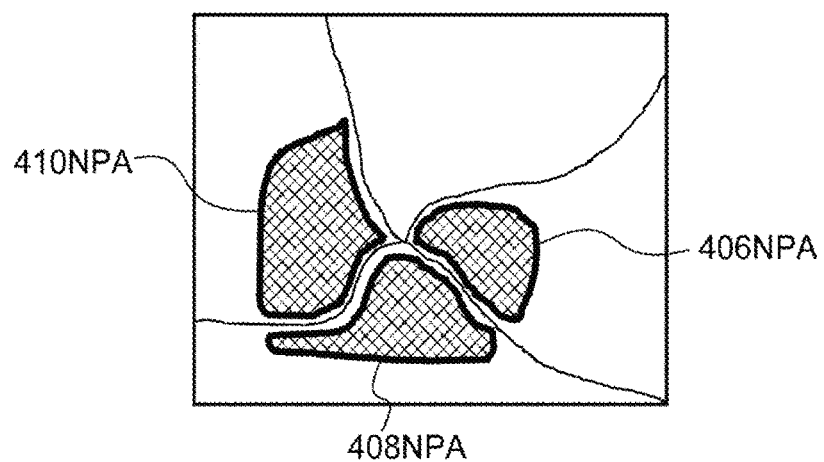
FIG. 17 is a diagram illustrating an appearance when shading of similar color to real color and different color to real color and has been applied to the predicted non perfusion areas 406NPA, 408NPA, 410NPA.

Furthermore, the non perfusion area candidate image may be generated by the generation section 208 applying light color shading (a color of a first density darker than the density of the UWFSLO image) to the predicted non perfusion areas 406NPA, 408NPA, 410NPA, as illustrated in FIG. 16. Note that at step 314, the generation section 208 may shade the predicted non perfusion areas 406NPA, 408NPA, 410NPA with a similar color to real color, or a different color to real color, as illustrated in FIG. 17. Note that broken lines may be employed for the borders at the periphery of the predicted non perfusion areas 406NPA, 408NPA, 410NPA.

The non perfusion area candidate image is an example of information employed by a doctor to diagnose or determine the progress of diabetic retinopathy, retinal vein occlusion, or the like.

At the next step 316, the transmission section 210 transmits the image data for the non perfusion area candidate image generated at step 314 to the image viewer 150.

On receipt of data for the non perfusion area candidate image, the image viewer 150 displays the non perfusion area candidate image on the display 156.

Figure 19:
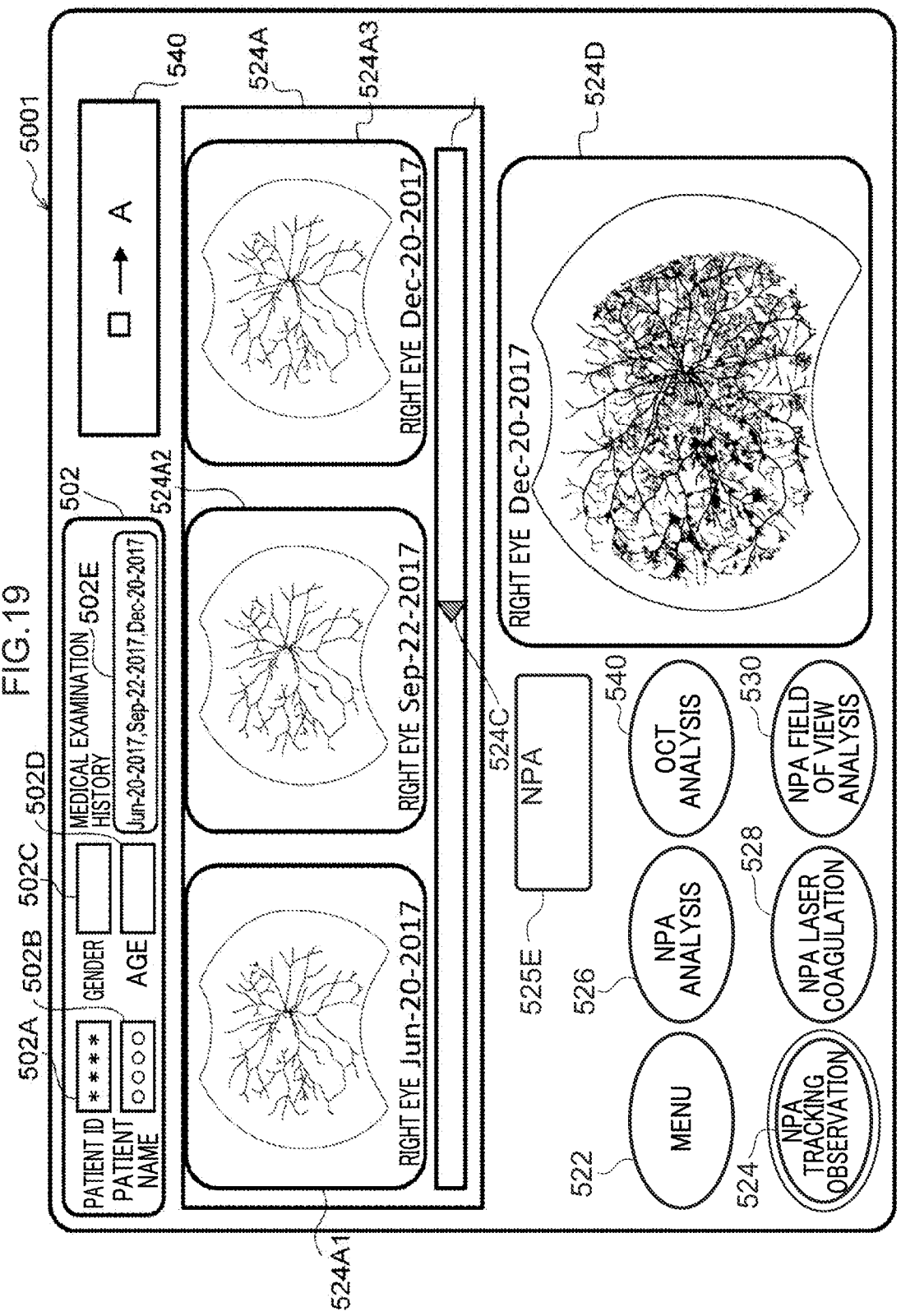
FIG. 19 is a diagram illustrating the screen 500 when an NPA tracking observation button 524 has been clicked.

Detailed description now follows regarding a method to display the non perfusion area candidate image, with reference to the screen 500 on the display 156 of the image viewer 150 as illustrated in FIG. 18 and FIG. 19.

The display methods illustrated in FIG. 18 and FIG. 19 are examples of an "image display method" of technology disclosed herein.

FIG. 18 illustrates a display content of an NPA analysis mode of the display 156 of the image viewer 150 displayed on the screen 500. The screen 500 includes a patient information display field 502, a UWFSLO image display field 504, an OCT image display field 506, a non perfusion area candidate image display field 508, and two enlarged image display fields 510, 512. The screen 500 also includes a menu button 522, an NPA tracking observation button 524, an NPA analysis button 526, an NPA laser coagulation button 528, an NPA field of view analysis button 530, and an OCT analysis button 540. Furthermore, the screen 500 also includes a tool button display field 540.

FIG. 18 illustrates a display screen for an NPA analysis mode and so, from out of the menu button 522, the NPA tracking observation button 524, the NPA analysis button 526, the NPA laser coagulation button 528, the NPA field of view analysis button 530, and the OCT analysis button 540, the NPA analysis button 526 is accordingly displayed in a first display state to indicate being active, and the other buttons are displayed in a second display state to indicate being inactive. The first display state and the second display state can be various display states, such as being displayed in different colors (e.g. the first display state green and the second display state red), being displayed in 3D (e.g. the first display state displayed in relief from the screen using shadow-display or the like, and the second display state displayed without shadows).

The patient information display field 502 includes a patient ID display field 502A, a patient name display field 502B, a gender display field 502C, an age display field 502D, and an attendance history display field 502E. The image viewer 150 acquires the patient ID, patient name, gender, age, and attendance history as stored in the management server 140. The image viewer 150 then displays the acquired patient ID, patient name, gender, age, and attendance history in the patient ID display field 502A, the patient name display field 502B, the gender display field 502C, the age display field 502D, and the attendance history display field 502E, respectively.

The image viewer 150 displays a UWFSLO image of the patient in the UWFSLO image display field 504 of the screen 500, and displays the non perfusion area candidate image in the non perfusion area candidate image display field 508 thereof.

In order to facilitate observation/diagnosis performed by a doctor, the non perfusion area candidate image is displayed in the non perfusion area candidate image display field 508 at a different magnification to the UWFSLO image displayed in the UWFSLO image display field 504. For example, the non perfusion area candidate image is displayed at a size of a specific magnification enlargement in comparison to the size of the UWFSLO image displayed in the UWFSLO image display field 504. The non perfusion area candidate image may also be displayed at a size shrunk by a specific magnification in comparison to the size of the UWFSLO image displayed in the UWFSLO image display field 504. Note that each of these specific magnifications may also be configured so as to be variable.

Situations arise in which the doctor wishes to see a portion in the non perfusion area candidate image in an enlarged view. Thus as illustrated in FIG. 18, for example, the doctor operates an input means such as a mouse to specify areas 508A, 508B desired to be viewed enlarged as areas within the non perfusion area candidate image display field 508 that the doctor wishes to display enlarged. When the areas 508A, 508B are specified, the image viewer 150 magnifies and displays images 508AA, 508BB that are portions of the specified areas 508A, 508B in the non perfusion area candidate image in the enlarged image display fields 510, 512.

In cases in which the doctor has viewed the non perfusion area candidate image and determined that an OCT image needs to be acquired, the doctor specifies a specified area 508C for acquiring an OCT image in the non perfusion area candidate image being displayed in the non perfusion area candidate image display field 508. The specified area may be a straight line or may be a rectangle. In such cases a specified area 504A may also be displayed on the UWFSLO image being displayed in the UWFSLO image display field 504 at a position corresponding to the 508C specified on the non perfusion area candidate image.

To specify the area 508C for acquiring an OCT image, an instruction to acquire the OCT image of the specified area 508C is output to an operator of the ophthalmic device 110 through the management server 140. A patient then revisits the room in which the ophthalmic device 110 is disposed. The ophthalmic device 110 acquires the OCT image in response to the instruction and transmits the OCT image to the management server 140. The OCT image data is then transmitted from the management server 140 to the image viewer 150, and the image viewer 150 displays the OCT image in the OCT image display field 506. The doctor accordingly checks the OCT image at the location where a problem in the subject eye 12 has been determined, and examines the subject eye 12.

Note that buttons to call various input aid tools are displayed in the tool button display field 540, such as an icon for displaying a line, an icon for displaying a rectangle, a text input icon to input text on the image, and a pen input icon or the like to display a handwritten sketch superimposed on the image.

The attendance history display field 502E is provided in the patient information display field 502. In the example illustrated in FIG. 18, attendance histories are being displayed for Jun. 20 2017, Sep. 22 2017, and Dec. 20 2017. A doctor who has determined that they wish to view the attendance history clicks on the NPA tracking observation button 524. When the NPA tracking observation button 524 is clicked, the screen 500 of the display 156 of the image viewer 150 is changed from the display state of the NPA analysis mode of FIG. 18 to the display state of an NPA tracking observation mode of FIG. 19.

As illustrated in FIG. 19, an NPA tracking observation mode screen 5001 includes a UWFSLO tracking image display field 524A, and a non perfusion area candidate image display field 524D in addition to the patient information display field 502 and the tool button display field 540. Note that patient information display field 502, the tool button display field 540, and the non perfusion area candidate image display field 524D are display fields similar to those of FIG. 18. FIG. 19 is a NPA tracking observation mode display screen, and so from out of the menu button 522, the NPA tracking observation button 524, the NPA analysis button 526, the NPA laser coagulation button 528, the NPA field of view analysis button 530, and the OCT analysis button 540, the NPA tracking observation button 524 is accordingly displayed in the first display state to indicate being active, and the other buttons are displayed in a second display state to indicate being inactive.

The UWFSLO tracking image display field 524A includes plural (three in the above example) tracking image display fields 524A1 to 524A3 for past UWFSLO images (tracking images), and a slider bar 524B including a slider 524C.

In cases in which the patient has attended four or more times, then a configuration might be considered in which all of four or more UWFSLO images are displayed at the same time. However, to display all the images the display field for each of the images would need to be made small, making it less visible. Thus the three tracking image display fields 524A1 to 524A3 are provided as described above. The position of the slider 524C is such that the right end corresponds to the current time, further to the left thereof corresponding to past times. The image viewer 150 is configured to displays three UWFSLO images that correspond to the position of the slider 524C in the tracking image display fields 524A1 to 524A3.

The doctor uses an input means such as a mouse to select an image desired for NPA analysis from out of the three UWFSLO images being displayed in the UWFSLO tracking image display field 524A. For example, when the tracking image 524A3 has been selected, the color of the border of 524A3 is displayed in a color different to the color of the borders of 524A1 and 524A2. The thickness of line for the border may also be changed instead of the color of the border, or both the color and the thickness of the border may be changed.

Next, the doctor presses (clicks on) the NPA prediction button 525E using a mouse or the like, and the image viewer 150 issues a command to the management server 140 so as to generate a non perfusion area candidate image for the selected tracking image 524A3. The management server 140 reads the image of the tracking image 524A3 and performs the image processing explained with reference to FIG. 6. The obtained non perfusion area candidate image corresponding to the tracking image 524A3 is saved in the storage device 154 of the management server, and image data for the image processed non perfusion area candidate image is transmitted to the image viewer 150.

The image viewer 150 displays the non perfusion area candidate image of the image processed tracking image 524A3 in the non perfusion area candidate image display field 524D of the screen 5001 based on the image data received for the non perfusion area candidate image of the image processed tracking image 524A3. The image viewer 150 may be configured to display the display border of the selected tracking image 524A3 and the display border of the non perfusion area candidate image display field 524D in the same color and line style or thickness.

Note that any of the three non perfusion area candidate images resulting from image processing the three UWFSLO images (tracking images) may be displayed in the non perfusion area candidate image display field 524D.

Moreover, if the doctor presses the NPA prediction button 525E without selecting a tracking image from out of the three UWFSLO tracking image display fields 524A, the image viewer 150 outputs a command to the management server 140 to generate non perfusion area candidate images for all of the UWFSLO images associated with the patient ID (namely, the 524A1, 524A2, 524A3 stored in an image folder for the patient ID). When there are, from out of the UWFSLO images stored in the image folder of the patient ID, UWFSLO images for which non perfusion area candidate images have already been generated, a command may be issued so as to generate non perfusion area candidate images for any UWFSLO images for which no non perfusion area candidate image has yet been generated.

The management server 140 sequentially reads the images of the tracking images 524A1, 524A2, 524A3, and performs the image processing explained with reference to FIG. 6 sequentially thereon. Then the obtained tracking image 524A3 is saved in the management server storage device 154, and the image data of the image processed non perfusion area candidate image is transmitted to the image viewer 150. The respective non perfusion area candidate images obtained for the tracking images 524A1, 524A2, 524A3 are each saved in the storage device 154 of the management server, and image data for the three new image processed non perfusion area candidate images are transmitted to the image viewer 150.

On receipt of the image data for the image processed three new non perfusion area candidate images, the image viewer 150 displays the three received non perfusion area candidate images in the UWFSLO image tracking image display fields of the screen 5001 based on the attendance history. Furthermore, when one non perfusion area candidate image has been selected from out of the three non perfusion area candidate images being displayed in the tracking image display fields, the selected non perfusion area candidate image is enlarged and displayed in the non perfusion area candidate image display field 524D. For example, in cases in which the non perfusion area candidate image 524A3 having the most recent attendance history has been selected, the display border of the non perfusion area candidate image 524A3 may be displayed in the same color and line style or thickness as the display border of the non perfusion area candidate image display field 524D.

Moreover, non perfusion area candidate images with different attendance dates may be compared, and image processing performed so as to display a newly appearing predicted non perfusion area in a changed color, and to display plural non perfusion area candidate images in the tracking observation image display fields. For example, the UWFSLO image imaged on Jun. 20 2017 displayed in 524A1 of FIG. 19 is processed to display the obtained predicted non perfusion areas in blue. Processing may be performed on the UWFSLO image imaged on Sep. 22 2017 displayed in 524A2 of FIG. 19 that enables, from out of the predicted non perfusion areas obtained thereby, predicted non perfusion areas that are predicted to be the same as the predicted non perfusion areas of Jun. 20 2017 to be displayed in blue, and predicted non perfusion areas appearing for the first time under the image processing of Sep. 22 2017 to be displayed in red. Such image processing enables valuable information for diagnosing the rate of progression of symptoms in a patient to be provided to a doctor, enabling support to be given to diagnosis.

Next description will be given regarding the function of the menu button 522, the NPA laser coagulation button 528, the NPA field of view analysis button 530, and the OCT analysis button 540 displayed on the screen 500 of FIG. 18 and on the screen 500I of FIG. 19.

The menu button 522 is a button to return to the menu screen of an ophthalmic electronic medical record. Tools for selecting initial settings and user recording, fundus observation mode, anterior segment diagnostic mode, and the like are displayed on the menu screen. Transition is made to the screen 500 of FIG. 18 when the "fundus observation mode" is selected on the menu screen.

The OCT analysis button 540 is a button for transitioning to a screen to perform image analysis using retinal tomographic images, a thickness map of the optic nerve layer, and the like obtained with the ophthalmic device 110, B scan data obtained by imaging the retina and OCT volume data.

The NPA laser coagulation button 528 is a button for transitioning to a screen to perform analysis related to treatment using the laser photocoagulator 130. In cases in which the result of diagnosis is that the doctor has determined there to be a pathological lesion on fundus of the patient and that there is a need to suppress pathological progression, sometimes treatment is performed to cause coagulation by illuminating a laser onto the fundus using the laser photocoagulator 130. The NPA laser coagulation button 528 is clicked in such cases. When the NPA laser coagulation button 528 is clicked, transition is made to a screen equipped with a simulation function so as to use the non perfusion area candidate image to present an appropriate laser illumination position in order to determine a position to illuminate the laser onto.

The NPA field of view analysis button is a button for transitioning to a screen to perform analysis related to the field of view using the field of view map (a map representing a visible range) obtained using the field of view measurement instrument 120 and the non perfusion area candidate image. When the NPA field of view analysis button 530 is clicked, transition is made to an NPA field of view analysis mode to combine and display the field of view map from the field of view measurement instrument 120 combined with the non perfusion area candidate image. Performing analysis processing in which the field of view map is combined with an image including enhanced non perfusion areas enables correlation between the position of the NPAs on the retina and the field of view to be investigated.

Advantageous Effect of Exemplary Embodiments

The present exemplary embodiment as described above enables non perfusion areas to be predicted by performing image processing on fundus images.

Moreover, due to plural non perfusion areas being predicted from a fundus image that has been subjected to enhancement image processing to enhance the vascular portions, the present exemplary embodiment also enables plural non perfusion areas to be predicted with good precision.

Furthermore, employing UWFSLO images to predict the non perfusion areas enables early stage discovery of NPAs in areas around the retina periphery, and enables not only diabetic retinopathy, but also retinal vein occlusion, and retinal artery occlusion to be discovered at an early stage.

Moreover, the present exemplary embodiment is also useful in specifying laser illumination positions for laser coagulation surgery using the laser photocoagulator 130. Furthermore, the present exemplary embodiment enables a correlation between NPAs and field of view to be investigated by performing analysis processing of the field-of-view examination data of the field of view measurement instrument 120, and the field-of-view examination data combined with an image in which the non perfusion areas have been enhanced.

Furthermore, performing successive observations of the non perfusion areas using tracking observations enables information to be provided to the doctor to support checking of the effects of treatment and the progression of symptoms.

MODIFIED EXAMPLES

First Modified Example

In the technology disclosed herein, either step 308 or step 310 may be executed first, with a group of non perfusion area candidates predicted thereby employed as secondary candidates, and then at the other step continuing therefrom, these secondary candidates may be narrowed down to tertiary candidates. For example, after executing the processing of step 308, the candidates resulting therefrom may be further narrowed down at step 310, or in reverse, after executing the processing of step 310, the candidates resulting therefrom may be further narrowed down at step 308. This enables step 312 to be omitted.

Moreover, the predicted non perfusion areas may be areas narrowed down by step 306 and step 308. The predicted non perfusion areas may also be areas narrowed down by step 306 and step 310.

Second Modified Example

In technology disclosed herein, the above described contents of the processing of step 312 may be modified, and as a consolidated step 312, the prediction processing section

206 may select plural areas that are at least dark areas or areas having blood vessels running alongside as a group of non perfusion area candidates.

Third Modified Example

In the above exemplary embodiment, at step 314, in the UWFSLO image a colored border is applied to the periphery of plural predicted non perfusion areas and light color shading is applied thereto. However, technology disclosed herein is not limited thereby, and an image may be generated that omits the vascular portions and indicates only plural non perfusion areas, or an image may be generated that omits the vascular portions and only includes plural non perfusion areas enhanced in the manner described above.

Fourth Modified Example

In the technology disclosed herein, information for display may also include left-right eye information, a graph of change over time in the number of non perfusion areas appearing, a graph of change over time in the average surface area of non perfusion areas, and a graph of change over time in the total surface area of non perfusion areas. Furthermore, during laser coagulation surgery, the non perfusion area candidate image may be displayed superimposed on the UWFSLO fundus image.

Fifth Modified Example

Although in the above exemplary embodiment the image processing program of FIG. 6 is executed by the management server 140, the technology disclosed herein is not limited thereto. For example, in a first case the image processing program of FIG. 6 may be stored in the storage device 17 of the ophthalmic device 110, and the ophthalmic device 110 execute the image processing program of FIG. 6 every time an UWFSLO image is acquired. In a second case the image viewer 150 may execute steps 302 to 314. Note that at step 302 in the second case, the image data of the specified fundus image is acquired from the management server 140, and instead of the content of step 316, an image in which plural non perfusion areas have been enhanced is displayed on the display 156. In the first case, the ophthalmic device 110 is an example of an image processing device of technology disclosed herein. In the second case, the image viewer 150 is an example of an image processing device of technology disclosed herein.

Sixth Modified Example

Although in the above exemplary embodiment the image viewer 150 displays on the display 156 the image in which plural non perfusion areas are enhanced, the technology disclosed herein is not limited thereto. For example, an UWFSLO image of FIG. 7, an image in which the blood vessels have been enhanced in the UWFSLO image of FIG. 8, or an image of plural enhanced non perfusion areas as in FIG. 15 to FIG. 17 may be displayed. In such cases, the images of FIG. 7, FIG. 8, and FIG. 15 to FIG. 17 may be displayed in a display array, may be displayed so as to be switched sequentially every time clicked, or may be selectively displayed.

Seventh Modified Example

In the technology disclosed herein the primary candidates for non perfusion area acquired at step 306, and the images of candidates removed from the candidates at steps 308, 310 may be displayed in a display array, may be displayed so as to be switched sequentially every time clicked, or may be selectively displayed.

Eighth Modified Example

Although in the above exemplary embodiment an image of the entire fundus is acquired as the UWFSLO image, technology disclosed herein is not limited thereto. An UWFSLO image of only a specific area including an already appearing pathological lesion may be acquired as a tracking observation.

Ninth Modified Example

Although an example has been described in which an UWFSLO image is subjected to image processing, obviously a fundus image from a fundus camera may be appropriately employed therefor, and fundus images imaged by various ophthalmic devices, such as an SLO ophthalmic device or fundus camera with relatively narrow angle (for example, an internal illumination angle of 100 degrees of less) may be appropriately employed therefor.

Tenth Modified Example

Although in the above exemplary embodiment an example has been described of the ophthalmic system 100 equipped with the ophthalmic device 110, the field of view measurement instrument 120, the laser photocoagulator 130, the management server 140, and the image viewer 150, the technology disclosed herein is not limited thereto. For example, as a first example the ophthalmic device 110 may further include at least one function from either the field of view measurement instrument 120 or the laser photocoagulator 130. Moreover, as a second example, the ophthalmic device 110 of the above exemplary embodiment may be equipped with the field of view measurement instrument 120 and the laser photocoagulator 130. In both the first example and the second example, the ophthalmic device 110 may further include at least one function of the management server 140 or the image viewer 150. Adopting such an approach enables at least one device from out of the management server 140 or the image viewer 150 to be omitted, i.e. the device corresponding to the function the ophthalmic device 110 is equipped with to be omitted.

Moreover, the management server 140 may be omitted, and the image viewer 150 configured so as to execute the function of the management server 140.

Note that the image processing described in the above exemplary embodiment is merely an example thereof. Thus obviously unnecessary steps may be omitted, new steps may be added, and the sequence of processing may be changed within a scope not departing from the spirit of technology disclosed herein.

Note that although in the above exemplary embodiment a case is presented as an example in which a computer is employed to implement data processing using a software configuration, the technology disclosed herein is not limited thereto. For example, instead of a software configuration employing a computer, the data processing may be executed using a hardware configuration alone, such as with FPGAs, ASICs, etc. Alternatively some processing in the data processing may be executed by a software configuration, and the remaining processing therein may be executed by a hardware configuration.

EXPLANATION OF REFERENCE NUMERALS

12 subject eye
100 ophthalmic system
110 ophthalmic device
120 field of view measurement instrument
130 laser photocoagulator
140 management server
150 image viewer
154 storage device
154P image processing program

The invention claimed is:

1. An image processing method comprising predicting a non perfusion area in a fundus image of a subject eye;
   wherein the predicting of a non perfusion area in the fundus image includes:
   extracting a plurality of dark pixels darker than a first darkness from the fundus image, and detecting from the plurality of extracted pixels an area having a surface area of a specific surface area or greater in which the dark pixels darker than the first darkness are contiguous,
   from areas having a surface area of the specific surface area or greater and based on an average value of pixel values for each of the areas, extracting a dark area of a second darkness darker than the first darkness, or darker than the second darkness,
   from areas having a surface area of the specific surface area or greater, extracting an area having blood vessels running alongside, and
   extracting an area that has been both extracted as the dark area and extracted as the area having blood vessels running alongside.

2. The image processing method of claim 1, further comprising generating a non perfusion area candidate image in which the predicted non perfusion area is superimposed on the fundus image.

3. The image processing method of claim 1, wherein:
   enhancement image processing is performed on the fundus image to enhance vascular portions; and
   a fundus image that has been subjected to the enhancement image processing is employed to predict the non perfusion area.

4. The image processing method of claim 3, further comprising generating a non perfusion area candidate image in which the predicted non perfusion area is superimposed on the fundus image that has been subjected to enhancement image processing.

5. A non-transitory storage medium storing an image processing program that causes a computer to execute the image processing method of claim 1.

6. An image processing device comprising:
   a storage device to store an image processing program for executing an image processing method in a processing device; and
   a processing device configured to execute the image processing method by executing the image processing program stored in the storage device;
   the image processing method being the image processing method of claim 1.

7. An image display device comprising a display section configured to display a non perfusion area predicted using the image processing method of claim 1.

* * * * *